US006509042B1

(12) United States Patent
Koren et al.

(10) Patent No.: US 6,509,042 B1
(45) Date of Patent: Jan. 21, 2003

(54) ANTI VIRAL COMPOSITION

(75) Inventors: Odelia Koren, 53/4 Meginei Hagalil St., Rehovot 76200 (IL); Sima Avrahami, Sireni Street 38, Rehovot 76229 (IL); Hadassa Bymel, Ahuza Haifa (IL)

(73) Assignees: Hadas Natural Products Ltd., Yoqneam Elite (IL); Odelia Koren, Rehovot (IL); Sima Avrahami, Rehovot (IL)

( * ) Notice: Subject to any disclaimer, the term of this patent is extended or adjusted under 35 U.S.C. 154(b) by 0 days.

(21) Appl. No.: 09/695,853

(22) Filed: Oct. 26, 2000

(30) Foreign Application Priority Data

Oct. 31, 1999 (IL) .................................................. 132665

(51) Int. Cl.$^7$ ............................................. A61K 91/14
(52) U.S. Cl. ....................................... 424/757; 424/776
(58) Field of Search .................................. 424/757, 776

(56) References Cited

U.S. PATENT DOCUMENTS

| 5,665,376 A | * | 9/1997 | Russo |
| 5,766,632 A | | 6/1998 | Oldham et al. |
| 5,840,771 A | | 11/1998 | Oldham et al. |

FOREIGN PATENT DOCUMENTS

| EP | 0 295 955 A2 | 12/1988 |
| EP | 0 462 020 A2 | 12/1991 |

OTHER PUBLICATIONS

Hamza et al. Qualitas Plantarum. 1987. vol. 36, No. 4, pp. 253–262, FSTA Abstract enclosed.*

Database Biosis 'Online! Biosciences Information Service, XP 002159179 , English language abstract of Krivorutchenko, Yu. L "Immunoadjuvant And Antiviral Properties Of Saponins" Voprosy Virusologii, V. 43, N. 1, pp. 7–10, (Jan.–Feb. 1998).

Database WPI, Derwent Publications Ltd., XP 002159180, Abstract of CN 1 074 614 A (Deng P), published Jul. 28, 1993.

Database WPI, Derwent Publications Ltd, XP 002159181, Abstract of JP 05 320061 A (Soken KK) published Dec. 3, 1993.

Database WPI, Derwent Publications Ltd, XP 002159182, Abstract of CN 1 103 313 A (Xu X), published Jun. 7, 1995.

* cited by examiner

Primary Examiner—Christopher R. Tate
(74) Attorney, Agent, or Firm—Browdy and Neimark

(57) ABSTRACT

Disclosed is a pharmaceutical composition., especially for treating herpes and condyloma, comprising an extraction product of broad beans, as an active ingredient.

18 Claims, No Drawings

ANTI VIRAL COMPOSITION

FIELD OF THE INVENTION

This invention relates to pharmaceutical and neutraceutical compositions, in particular such compositions for treating skin viral injuries, e.g. such inflected by herpes or condyloma.

BACKGROUND OF THE INVENTION

Herpes is a viral infection that causes painful sores (usually near the mouth or the genitals). There are several known pharmaceutical compositions for treating herpes, which usually make the sores disappear within a week. However, the sores come back from time to time, and when they disappear they leave a scar. In some patients the efficiency of a specific medication decreases when continuously used.

Condyloma is a painful viral callus of the genitals. Conventionally it is treated by surgery, but it often recurs thereafter.

Broad beans (also known as Fava beans) are known as food and as a source for lectins. Lectins are carbohydrate binding proteins of noninmune origin that agglutinate cells or precipitate proteins or lipids conjugated to oligo- or polysaccharides. U.S. Pat. No. 5,766,632 and U.S. Pat. No. 5,840,771 describe the use of lectins (optionally derived from broad bean) for contraception and as anti STD (Sexually Transmitted Diseases) agent.

SUMMARY OF THE INVENTION

According to the present invention it was found that extraction products of broad beans have a pharmaceutical activity, and are particularly active for the treatment of herpes and condyloma.

The term "treatment" as used herein should be understood as meaning both preventive and acute treatment. Acute treatment is the administration of the composition during the course of disease or during the course of appearance of symptoms associated therewith. A preventive treatment is a treatment given to an individual prior to occurrence of a disease or prior to appearance of symptoms associated therewith, in order to reduce the frequency of its occurrence, reduce its severity or reduce severity of the symptoms, A preventive treatment may also be a treatment to an individual after an acute disease phase in order to decrease the chance of the recurrence of the disease or reduce the severity of the disease or symptoms associated therewith.

Thus, according to one aspect of the invention, there is provided a pharmaceutical composition comprising, as an active ingredient, an effective amount of an extraction product of broad beans.

According to another aspect of the invention, there is provided a method for treating of a disease or disorder, comprising administering to a subject in need an effective amount of extraction products of broad beans.

In accordance with a still further aspect of the invention there is provided use of an exaction product of broad beans, for the preparation of a pharmaceutical composition.

Still further provided by the invention is an extraction product of broad beans for use in the treatment of a disease or disorder in a subject or for the preparation of a pharmaceutical composition for use in such treatment.

Further provided by the invention is a process for the preparation of a pharmaceutically active ingredient, which comprises the steps of:

(i) providing broad bean;
(ii) roasting said broad bean;
(iii) grinding the roasted broad bean; and
(iv) steeping the ground roasted broad bean in an alcoholic solution.

A preferred embodiment of the invention is concerned with its treatment or prevention of herpes infection or condyloma sores. Typically, in accordance with this embodiment, but not exclusively, the active ingredient will be formulated as a topical composition, e.g. in the form of a gel, ointment, salve, solution, etc., to be applied onto skin portions where sores or infection wounds appear. In accordance with another embodiment, the active ingredient will be formulated in the form of an oral composition, particularly as a mouth-wash for treatment of a variety of viral diseases causing sores, wounds or lesions within the mouth.

The term "effective amount" should be understood as meaning the amount of an active ingredient sufficient to yield a desired medicinal effect. The effective amount of the active ingredient may depend on the type of indication, the manner in which the active ingredient is formulated as well as on the dosage form. For example, in the case of topical formulation for the treatment of herpes or condyloma infections, the effective amount is an amount sufficient to give rise to reduction in the time period in which the wounds or sores are present, reduction in their severity, reduction in the probability of a recurring or de novo infection, etc.

As readily known, the effective amount may vary also depending on the individual's age, gender, weight, other treatments to which the individual is subjected to, the stage of disease, etc.

It should be noted that the term "pharmaceutical composition" should be construed in a broad sense and includes any composition which is intended for the purpose of achieving a therapeutic effect whether sold as a pharmaceutical product, for example carrying a label as to the intended indication, whether sold over the counter without any specific indication, or whether sold as a neutraceutical (neutraccuticals are at times also referred to in the art as "food additives" or "nutritional supplements").

The extraction product may be obtained from the broad bean by a variety of extraction methods and the invention is not limited to the extraction method used. The pharmaceutically active ingredient in accordance with the invention may be obtained by roasting the broad beans, grinding the beans, steeping the ground solid matter in a polar and protic extracting liquid, typically an alcoholic solution, e.g. a solution of 70% ethanol in water. The alcoholic solution so obtained by then serve as the active ingredient as such. Alternatively, is Tact may be fractionated to obtain a pharmaceutically active fraction, such as, for example, by chromatography, e.g. high pressure liquid chromatography (BPLC), by phase separation technirques, etc. In addition, the alcoholic extract or fractionation product may be processed to obtain therefrom the active ingredient in a dry form, e.g. by lyophilization. Fractionation and drying techniques are all known per se and will not be elaborated further herein.

Any polar protic solvent may serve as an extracting liquid. In case water is used, it is preferable to cook the roasted broad beans in boiling water for about two hours and then to distill it. The distilled vapor is cooled to provide the active ingredient.

Preferably, the extracting liquid should be a pharmaceutical grade liquid. Particularly, if the solvent or fractions thereof will remain in the pharmaceutical composition which is intended for oral administration, the solvent should be such which is permitted for oral administration.

Although grinding is helpful to increase the efficiency of the extraction, the active ingredient may be obtained without it. In such a case longer periods of steeping, and, possibly, higher extraction temperatures may be needed in order to obtain the active ingredient in a similar concentration to that obtained after grinding.

The steeping is preferably for a period of about two weeks with daily shaking. It is preferable to separate the residue from the solution before using the solution.

A liquid extraction product containing the active ingredient may be used as such as already indicated above, or may be supplemented with varieties of excipients and carriers suitable for the intended mode of administration of the composition. For example, in the case of a topical composition, the liquid extraction product may be combined with gelling agents to yield a gel intended for topical application.

At times, the composition may also contain additional active or non-active ingredients. Non-limiting examples of such ingredients are a variety of plant extracts such as Echinacea, chamomile, *mellisa calendula* and *propolis*.

DETAILED DESCRIPTION OF A PREFERRED EMBODIMENT

In order to understand the invention and to see how it may be carried out in practice, a preferred embodiment will now be described, by way of non-limiting example only.

1 kg of broad beans of the species *vicia faba* were roasted in an oven at 200° C. until they became dark brown. The roasted beans were ground to coarse powder and steeped in 4 liters of 70% Ethanol in water for two weeks, shaking the solution daily. The solution was then filtered on a regular filter paper to obtain an alcoholic solution that was applied to the sores either as is or as a jell, containing 70% of the solution and the rest regularly used excipients and carriers suitable for topical administration.

For the preparation of a jell, 700 ml of a solution containing the above-mentioned alcoholic solution of the broad bean extract and extracts of aloe vera, echinacea purpurea, chamomile, melissa officinalis, propolis, and calendula officinalis were mixed for thirty minutes with 300 ml of a completely homogeneous mixture of propylene glycol, methylparaben, glycerin, hyaluronic acid, disodium EDTA and imidazolidinyl urea. 10 gr of Vitamin E were added during mixing.

The solution and the jell were used on human volunteers that suffered from herpes or condyloma with excellent results: the herpes sores left without leaving scars, after only two or three days and reappeared after periods that were longer usual for the patients. The condyloma sores disappeared within 7 to 30 days and an operation was no longer needed.

What is claimed is:

1. A pharmaceutical composition effective in topically treating viral skin infections, comprising,
    as an active ingredient, an effective amount of an extract obtained by extracting roasted broad beans in an extracting liquid,
    with the proviso that if the extracting liquid is water, the pharmaceutical composition further comprises at least one additional pharmaceutically acceptable excipient or carrier suitable for topical administration of the pharmaceutical composition.

2. A pharmaceutical composition according to claim 1, wherein said extracting liquid comprises an alcohol.

3. A pharmaceutical composition according to claim 1, wherein said extracting liquid is water.

4. A pharmaceutical composition according to claim 1, wherein said broad beans are of the species vicia faba.

5. A pharmaceutical composition according to claim 1 in the form of an ointment, salve, gel or liquid solution.

6. A pharmaceutical composition according to claim 1 in a dosage form suitable for treatment of herpes.

7. The pharmaceutical composition of claim 6 in the form of a mouthwash.

8. The pharmaceutical composition of claim 6 in the form of an ointment, salve or gel.

9. A pharmaceutical composition according to claim 1 in a dosage form suitable for treatment of condyloma.

10. The pharmaceutical composition of claim 9 in the form of an ointment, salve or gel.

11. A pharmaceutical composition according to claim 2, prepared by a process comprising the steps of:
    (i) providing broad beans;
    (ii) roasting said broad beans;
    (iii) grinding the roasted broad beans; and
    (iv) steeping the ground roasted broad beans in an alcoholic solution.

12. A pharmaceutical composition according to claim 11 wherein said process comprises the further steps of:
    (v) separating the solid residue from said alcoholic solution; and, optionally,
    (vi) discarding the solid residue.

13. A pharmaceutical composition according to claim 3 prepared by a process comprising:
    (i) providing broad beans;
    (ii) roasting said broad beans;
    (iii) grinding the roasted broad beans;
    (iv) cooking the ground roasted beans in boiling water;
    (v) distilling said water;
    (vi) cooling the vapor thus distilled to obtain an active ingredient;
    (vii) formulating the active ingredient obtained in (vi) into a pharmaceutical composition.

14. A pharmaceutical composition according to claim 13 wherein (vii) includes mixing the active ingredient obtained in (vi) with a carrier suitable for topical administration.

15. A method for the treatment of viral infections, wherein said treatment comprises topical administration of a pharmaceutical composition according to claim 1 comprising a therapeutically effective amount of said extract to a patient in need of such treatment.

16. A method according to claim 15 wherein said viral infection is heroes.

17. A method according to claim 15 wherein said viral infection is condylotna.

18. A pharmaceutical composition for topically treating viral skin infections comprising, as an active ingredient, an effective amount of an extract obtained by extracting roasted broad beans in an extracting liquid,
    with the proviso that if the extracting liquid is water, the pharmaceutical composition further comprises at least one additional pharmaceutically acceptable excipient or carrier suitable for topically treating viral skin infections.

* * * * *